US012752088B2

(12) United States Patent
Brohm-Schmitz-Rode et al.

(10) Patent No.: US 12,752,088 B2
(45) Date of Patent: Oct. 6, 2026

(54) BALLOON CATHETER DEVICE FOR ATRAUMATIC EXPANSION OF HOLLOW ORGANS, AND A METHOD FOR PRODUCING SUCH A BALLOON CATHETER DEVICE

(71) Applicant: BVS—BEST VASCULAR SOLUTIONS GMBH, Bonn (DE)

(72) Inventors: Andrea Brohm-Schmitz-Rode, Aachen (DE); Thomas Schmitz-Rode, Aachen (DE)

(73) Assignee: BVS—BEST VASCULAR SOLUTIONS GMBH, Bonn (DE)

( * ) Notice: Subject to any disclaimer, the term of this patent is extended or adjusted under 35 U.S.C. 154(b) by 0 days.

(21) Appl. No.: 18/993,667

(22) PCT Filed: Jul. 21, 2023

(86) PCT No.: PCT/EP2023/070364
§ 371 (c)(1),
(2) Date: Jan. 13, 2025

(87) PCT Pub. No.: WO2024/018082
PCT Pub. Date: Jan. 25, 2024

(65) Prior Publication Data

US 2025/0262417 A1 Aug. 21, 2025

(30) Foreign Application Priority Data

Jul. 22, 2022 (DE) ..................... 10 2022 118 449.8
Sep. 6, 2022 (DE) ..................... 10 2022 122 630.1

(51) Int. Cl.
*A61M 25/10* (2013.01)
*A61M 25/00* (2006.01)

(52) U.S. Cl.
CPC .... *A61M 25/1029* (2013.01); *A61M 25/0045* (2013.01); *A61M 25/1036* (2013.01);
(Continued)

(58) Field of Classification Search
CPC .......... A61M 25/1029; A61M 25/0045; A61M 25/1036; A61M 25/1002; A61M 25/104;
(Continued)

(56) References Cited

U.S. PATENT DOCUMENTS 5,443,495 A 8/1995 Buscemi et al.
5,507,770 A 4/1996 Turk
(Continued)

FOREIGN PATENT DOCUMENTS

CN 111107889 A 5/2020
DE 102006020687 A1 2/2007
(Continued)

OTHER PUBLICATIONS

International Preliminary Report on Patentability, mailed on Feb. 6, 2025, from International Application No. PCT/EP2023/070364, filed on Jul. 21, 2023. 12 pages.
(Continued)

*Primary Examiner* — James D Ponton
*Assistant Examiner* — John A Doubrava
(74) *Attorney, Agent, or Firm* — HoustonHogle LLP

(57) ABSTRACT

According to the invention, a balloon catheter device for the atraumatic treatment of hollow organs is provided. It comprises a balloon catheter with a balloon,
a tubular functional sleeve applied to the balloon for the directed segmented cushion-like unfolding of the balloon for the dilation of a hollow organ and simultaneous application of active substance into the hollow organ wall, and wherein (Continued)

Figure 1:
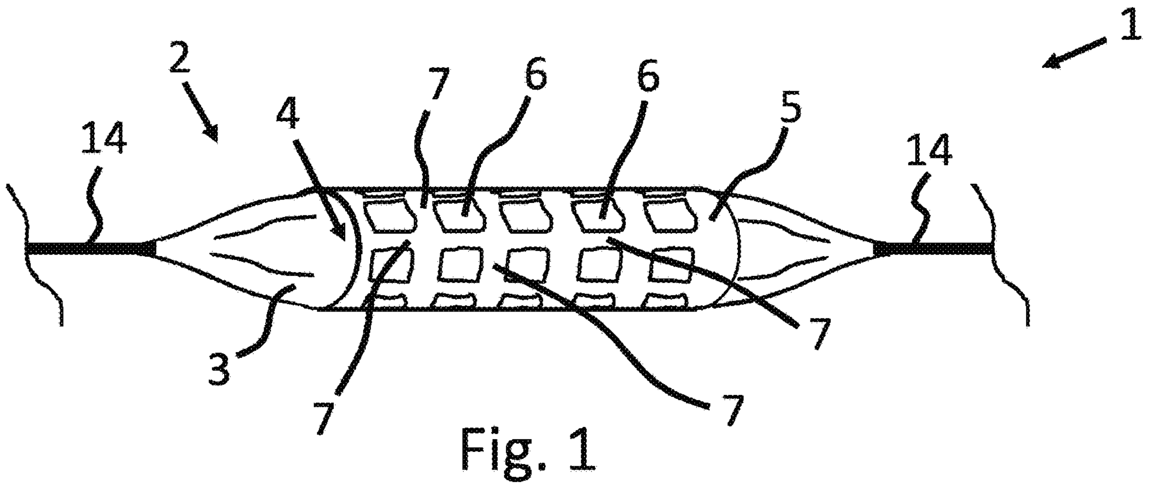

the functional sleeve is folded in an initial state together with the balloon about a sleeve longitudinal axis, and wherein the folding of the functional sleeve is directed as pleating about a sleeve longitudinal axis and in a final state is unfoldable for abutting against an inner wall of a hollow organ, and wherein the tubular functional sleeve has planar sections and/or planar struts which delimit through-openings, so that the functional sleeve is used for sectional limitation of a balloon dilation of the balloon.

6 Claims, 5 Drawing Sheets

(52) U.S. Cl.
CPC ............... *A61M 2025/0057* (2013.01); *A61M 2025/1031* (2013.01); *A61M 2025/105* (2013.01); *A61M 2025/1084* (2013.01); *A61M 2025/1086* (2013.01); *A61M 2205/0238* (2013.01); *A61M 2207/00* (2013.01)

(58) Field of Classification Search
CPC .. A61M 2025/0057; A61M 2025/1031; A61M 2025/105; A61M 2025/1084; A61M 2025/1086; A61M 2025/1004; A61M 2025/1059; A61M 2205/0238; A61M 2207/00
See application file for complete search history.

(56) References Cited

U.S. PATENT DOCUMENTS

| | | | | |
|---|---|---|---|---|
| 5,810,767 | A | 9/1998 | Klein | |
| 6,059,823 | A | 5/2000 | Holman et al. | |
| 11,000,680 | B2 | 5/2021 | Konstantino et al. | |
| 2002/0045930 | A1 | 4/2002 | Burg et al. | |
| 2005/0090888 | A1 | 4/2005 | Hines et al. | |
| 2005/0125053 | A1 | 6/2005 | Yachia et al. | |
| 2005/0149175 | A1* | 7/2005 | Hunter | A61F 2/86 623/1.42 |
| 2005/0182361 | A1 | 8/2005 | Lennox | |
| 2006/0135985 | A1 | 6/2006 | Cox et al. | |
| 2008/0262594 | A1 | 10/2008 | Morris | |
| 2009/0227948 | A1* | 9/2009 | Chen | A61L 29/16 604/103.05 |
| 2010/0249946 | A1 | 9/2010 | Lesh et al. | |
| 2014/0066960 | A1 | 3/2014 | Feld et al. | |
| 2014/0239558 | A1 | 8/2014 | Wang et al. | |
| 2019/0231565 | A1* | 8/2019 | Brohm-Schmitz-Rode | A61F 2/958 |

FOREIGN PATENT DOCUMENTS

| | | | |
|---|---|---|---|
| DE | 102005056529 | A1 | 5/2007 |
| DE | 102012007640 | A1 | 10/2013 |
| EP | 3922217 | A1 | 12/2021 |
| WO | WO 2002076700 | A1 | 10/2002 |
| WO | WO 2016151035 | A1 | 9/2016 |

OTHER PUBLICATIONS

International Search Report and Written Opinion of the International Searching Authority, mailed on Nov. 29, 2023, from International Application No. PCT/EP2023/070364, filed on Jul. 21, 2023. 12 pages.

Katsanos, K., et al., "Risk of Death Following Application of Paclitaxel-Coated Balloons and Stents in the Femoropopliteal Artery of the Leg: A Systematic Review and Meta-Analysis of Randomized Controlled Trials", Journal of American Hear Association, 7 (24):e011245 (2018).

* cited by examiner

BALLOON CATHETER DEVICE FOR ATRAUMATIC EXPANSION OF HOLLOW ORGANS, AND A METHOD FOR PRODUCING SUCH A BALLOON CATHETER DEVICE

RELATED APPLICATIONS

This application is a § 371 National Phase Application of International Application No. PCT/EP2023/070364, filed on Jul. 21, 2023, now International Publication No. WO 2024/018082, published on Jan. 25, 2024, which International Application claims priority to German Application 10 2022 118 449.8, filed on Jul. 22,2022 and to German Application 10 2022 122 630.1, filed on Sep. 6, 2022, all which are incorporated herein by reference in their entirety.

The present invention relates to a balloon catheter device (balloon catheter with functional sleeve) and a method for manufacturing such a balloon catheter device with functional sleeve.

Dilation of constrictions in hollow organs using balloon catheters is an integral part of minimally invasive therapy. This applies in particular to blood vessels. As part of endovascular therapy, atherosclerosis-related constrictions and occlusions of blood vessels are treated by balloon dilation.

Typically, a balloon catheter is inserted into the vascular system under imaging guidance. After placing the balloon in the area of the lesion to be treated, the balloon is expanded under high pressure. However, this standard treatment can cause serious complications. The balloon dilation causes damage to the vessel wall.

Typically, longitudinal ruptures occur in the vessel wall. This injury may cause clots in the first few days after treatment. In the following days up to a period of about three months, the blood vessel wall reacts to the dilation trauma with an excessive wall reaction. Smooth muscle cells in the vessel wall are stimulated by the trauma and produce extracellular matrix ("intimal hyperplasia"). The associated increase in volume in the vessel wall leads to a renewed formation of a constriction and thus counteracts to the treatment result. Even the implantation of a vascular support (stent) to permanently widen the vessel may not prevent this. A stent is a foreign body that can have a clot-forming effect on the one hand, while on the other hand its rigidity blocks the natural pulsatile motility of the stent-supplied vessel section and thus exerts a constant stimulus on the vessel wall. This stimulus can in turn lead to excessive production of the vessel wall cells with ingrowth of the tissue through the stent struts and thus to the formation of a new constriction.

For this reason, the stents being currently usually implanted are coated with an antiproliferative agent that reduces cell stimulation and matrix production. In the case of mere balloon dilatation without stent implantation, balloon catheters are currently predominantly used whose balloon sleeve is coated on the outside with an equivalent antiproliferative agent that is to be transferred to the vessel wall during balloon dilation. The coating usually is made of a homogeneous film-like cover of the outer balloon membrane, including the active substance embedded in a carrier material (binder, "exipient"). The therapeutic goal is a supply of a therapeutic dose of an agent to the vessel wall for the critical period of 6 weeks to a maximum of 3 months for suppressing the excessive vessel wall reaction (Katsanos et al., J Am Heart Assoc 2018).

In particular, WO 2016/151035 A1 describes a tubular sleeve for the atraumatic treatment of hollow organs. The sleeve is intended to be ejected by means of a balloon catheter so that the sleeve remains in the hollow organ as an implant. Thus, separating the sleeve from the balloon membrane occurs during unfolding of the balloon.

US 2014/0239558 A1 describes a combination of "injection molding" and "blow molding" followed by laser cutting. As a result, a polymer stent such as the so-called "Esprit stent" is to be formed, which opens its cells like a regular stent when being unfold on a balloon. Furthermore, it is provided to eject the stent from a balloon after an unfolding of the balloon catheter.

US 2005/0182361 A1 describes a sleeve made of an elastic material to protect an underlying layer of an active ingredient. The elastic sleeve is placed over the folded balloon of the balloon catheter. The unfolded sleeve lies elastically over the folded balloon membrane and is stretched by the unfolding balloon. As the balloon unfolds, there is a significant increase in the circumference of the sleeve, with slits forming diamond-shaped windows. The purpose of the device is to protect the active ingredient layer.

CN 1 11 107 889 A discloses a balloon catheter on which a coating with a layer of a medical active ingredient is arranged. The active ingredient layer or the coating is enclosed by a sleeve to protect the active ingredient. The sleeve can be connected to a catheter shaft. The cover and the sleeve are not folded, only the balloon is folded. The cover can be rolled up to enable the application of different active ingredients.

EP 3 922 217 A1 discloses a tubular nonwoven structure as an active substance carrier (referred to as "sleeve" for short) for the atraumatic treatment of hollow organs, in particular for balloon dilation, wherein the sleeve is folded about a longitudinal axis of the sleeve in an initial state and can be unfolded in a final state to lie against an inner wall of a hollow organ, wherein the tubular sleeve is formed from at least first biodegradable polymer nanofibers and the folding of the sleeve is directed as pleating about a longitudinal axis of the sleeve, wherein a medical active ingredient is embedded in the first polymer nanofibers and/or is arranged in spaces between the polymer nanofibers, and wherein the first polymer fibers are designed such that they degrade as slowly biodegradable polymer nanofibers (PL) over an adjustable period of 2 weeks to 3 months, so that the active ingredient can be released to a hollow organ wall during this period. The tubular sleeve is formed from at least the first and second biodegradable polymer nanofibers.

U.S. Pat. No. 11,000,680 B2 describes a balloon catheter device with an expandable balloon surrounded by a "cage" of axially and tangentially extending nitinol wires. This cage creates multiple small cushions when the balloon membrane is expanded, which are intended to exert a better distribution of force on the vessel wall and thus reduce vessel wall trauma compared to a conventional balloon.

Similar devices and methods are known from DE 10 2012 007 640, WO 02 076 700 A1, U.S. Pat. No. 5,443,495 A1, DE 10 2006 020 687 A1, US 2005/0 090 888 A1, DE 2005 056 529, US 2002/0 045 930 A1, US 2005/0 125 053 A1, US 2008/0 262 594, U.S. Pat. Nos. 5,507,770 A, 6,059,823 A and US 2010/249946 A1.

The object of the present invention is to provide a medical instrument or device for an atraumatic treatment of hollow organs, which represents an alternative to the medical devices known from the prior art.

WO 2016/151035 A1 and EP 3 922 217 A1 show a tubular sleeve and a tubular non-woven structure as an active substance carrier, which can be ejected by means of a balloon of a balloon catheter.

In addition, a process for manufacturing such a medical instrument is provided.

These objects are solved with a device according to patent claim 1 and methods according to patent claims 14 and 15. Advantageous embodiments thereof are given in the dependent claims.

According to the invention, a balloon catheter device for atraumatic expansion of hollow organs is provided.

This comprises a balloon catheter with a balloon, a tubular planar functional sleeve applied to the balloon for directional segmented cushion-like unfolding of the balloon, and wherein the functional sleeve is folded in an initial state together with the balloon about a sleeve longitudinal axis, and wherein the folding of the functional sleeve is directed as pleating about a sleeve longitudinal axis and can be unfolded in a final state for abutment against an inner wall of a hollow organ, and wherein the tubular functional sleeve has planar sections and/or planar struts which delimit through openings, so that the functional sleeve delimits a balloon dilation of the balloon in sections, and wherein the functional sleeve is connected to the balloon in the region of the planar sections and/or the planar struts.

Atraumatic treatment of hollow organs can be understood to mean, on the one hand, an expansion of a hollow organ in which a hollow organ is expanded. On the other hand, a temporary implantation may be provided by which a medical agent is applied. Such a time-limited application extends over a period of at least two or at least three to a maximum of 5 or 10 minutes. A simultaneous release of the active ingredient into the hollow organ wall generally lasts for weeks to months.

Due to the flat sections and/or flat struts that delimit the through-openings, the functional sleeve enables the balloon to be expanded in a limited and, in particular, reinforced manner, so that a uniform cushion formation of the balloon in the area of the through-openings occurs. In this way (compared to conventional balloons) a more even contact and a more even distribution of force on the hollow organ or blood vessel wall is achieved during the balloon dilation. As a result, large circumscribed traumas of the wall and corresponding ruptures can be reduced.

In particular, the flat functional sleeve with through-openings reduces or prevents the formation of local stress peaks between the balloon sleeve and the vessel wall during the unfolding process, so that large ruptures in the vessel wall may no longer occur during balloon dilation.

The area in which the cushions are formed is referred to below as the first functional area.

In contrast to the balloon catheter device according to the invention, a wire cage, as described for example in U.S. Pat. No. 11,000,680 B2, also exerts trauma on the vessel wall due to local denting combined with shearing during the unfolding process. In addition, the wire cage significantly increases the insertion diameter of a balloon catheter device.

The sleeve according to the invention is connected to the balloon membrane and can be folded and unfolded together with the balloon membrane of the balloon catheter. However, the sleeve according to the invention does not have any micro-compartments, but rather through-openings which are window-like and/or in the form of slits.

The advantage of flat struts of the functional sleeve compared to a wire structure for segmentation of the balloon unfolding lies in a lower profile formation during folding, so that a smaller diameter of an insertion catheter may be provided. A low-profile insertion catheter facilitates the application. In addition, a wire formation during balloon unfolding can lead to additional hollow organ wall damage due to a combination of wire denting and shearing.

The functional sleeve according to the invention is thus segmented or has a grouped arrangement of through-openings (windows, slits) in such a way that the functional sleeve in the unfolded state has a contact surface on its outer contour opposite the hollow organ wall in the form of plate-shaped or planar sections or struts.

In the context of the present invention, the term "planar" is understood to mean that the tubular sleeve itself and also the struts and sections forming the tubular sleeves have a greater extension in an area parallel to the balloon surface of the balloon compared to a thickness orthogonal to the balloon surface.

According to the invention, it is thus provided that the sleeve is connected to the balloon membrane essentially over the entire length of the sleeve in the axial direction and is first folded together with the balloon membrane and then also unfolded together with the balloon membrane. This means that the sleeve always remains on the balloon membrane and is removed from a hollow organ together with the latter after a cushion-shaped balloon dilation of the hollow organ, combined with an application of active substance into the hollow organ wall.

A connection between the balloon and the sleeve is preferably made by adhesion of an adhesive layer containing an active substance, e.g. a gel, which is arranged between the balloon or the balloon membrane and the functional sleeve. Additionally, or alternatively, a punctiform and/or linear connection by laser welding or a planar connection by adhesive bonding, in particular a connection across all planar surfaces or struts, can be provided.)

In particular, the functional sleeve has a higher rigidity with approximately the same wall thickness or a higher modulus of elasticity than the balloon membrane.

In this way, the cushion-like unfolding is considerably favored. This means that the sleeve should be more rigid than the balloon membrane in order to be able to exert a circumferential limiting effect on the expanding balloon membrane in the area of its surfaces/struts. This creates the ideal cushion effect. It is also conceivable that the expansion stiffness of the sleeve and balloon membrane could be approximately the same or even slightly less.

In particular, a medical active ingredient layer may be arranged between balloon of the balloon catheter and the functional sleeve.

A corresponding release of the medical agent to a vessel wall may then occur in the area of the passage openings.

This area is referred to as the second functional area and corresponds to the size of the first functional area.

The planar sections and/or planar struts ensure that the medical active ingredient layer, which may be arranged under the functional sleeve, is protected, particularly when folding in the balloon catheter device for low-profile storage and during transportation to the site of action.

The sleeve preferably has a diameter that corresponds approximately to the diameter of the unfolded or expanded balloon.

The through openings can be formed as slits, in particular laser-cut slits, for the application of medicaments or active substances, wherein sections with axial slits, which are referred to as axial sections, and sections with tangential slits, which are referred to as tangential sections, can be formed alternately in the functional sleeve in an axial direction of the functional sleeve, and wherein the axial sections and the tangential sections form the first functional area and are formed at a distance from one another.

The provision of alternately arranged axial sections with corresponding axial slits and tangential or radial sections with corresponding tangential sections results in a constant or essentially uniform expansion of a diameter of the sleeve and the balloon in the axial direction in accordance with the invention.

The tangential sections form decoupling sections between the axial sections in order to enable an approximately constant diameter in the radial direction over a substantially entire length of the device in the axial direction.

In particular, the axial sections and the tangential sections are designed in an axial direction and arranged at a distance from each other in such a way that they do not overlap.

Furthermore, the axial slits of the axial sections and the tangential slits of the tangential sections can be designed and arranged in such a way that they do not overlap in the tangential direction. This means that neither the axial slits are arranged offset to each other nor are the tangential slits arranged offset to each other.

In the prior art, slits are often arranged offset to one another. According to the invention, the axial slits may be of the same design with respect to length and width and may be arranged circumferentially at approximately the same distance from and tangentially aligned with one another. Furthermore, according to the invention, the tangential slits may be of the same design in terms of length and width and may be arranged tangentially circumferentially at approximately the same distance from and tangentially aligned with one another.

The inventors of the present invention have recognized that such an arrangement of similar axial and tangential slits alternating along a sleeve axis or in the axial direction enables optimum or improved cushion formation. Since the balloon catheter device has a cylindrical shape, the wall tension in the functional sleeve under balloon pressure is twice as high in the tangential direction as in the axial direction (boiler formula). The axial slits expand under internal balloon pressure. The rather small expansion of each individual axial slit adds up around the circumference of the sleeve, resulting in an effective cushion-like expansion of the diameter. There is no significant expansion in the area of the tangential slits, resulting in a relative constriction around the circumference of the sleeve. However, the active ingredient can still be applied via the tangential slits, just as of course in the area of the axial slits.

The decoupling sections formed by the tangential sections cause the balloon to constrict in these areas so that an essentially constant diameter is provided in the axial sections. This leads to a uniform distribution of forces in a radial direction towards the outside. In this way, any resulting trauma to the hollow organ is kept to a minimum, as only smaller and more evenly distributed ruptures occur in the wall of the hollow organ.

In contrast to known devices, in which a bulbous or balloon-like or approximately spherical expansion occurs, the device according to the invention has an essentially cylindrical expansion in the axial direction.

It may be provided that the sleeve has alternating axial and tangential sections in the axial direction.

Because the balloon and the sleeve are connected to each other in their connection areas, the balloon catheter device is designed in such a way that the functional sleeve and the balloon are folded together or can be folded together by folding along formed folding lines during balloon deflation and when the sleeve is removed from a hollow organ.

The entire functional sleeve and thus the planar struts or planar sections forming the functional sleeve can have pores which have the task or are designed to release the underneath located active substance to the outside of the hollow organ wall when being unfolded, but do not have a cushion-forming effect.

The pores can have a diameter of around 50 μm to 100 μm.

A corresponding release of the active medical ingredient to a vessel wall may then occur in the entire area of the sleeve surface, i.e. in the area of the through openings or in the area of the cushions as well as via the pores in the area of the flat struts.

According to one such embodiment, the second functional area extends over the entire circumferential wall of the functional sleeve and is therefore advantageously enlarged accordingly, so that the active medical ingredient can be released over a larger area and/or so that more active ingredient can be released.

The medical active ingredient layer can be formed together with a polymer, for example a biodegradable polymer, or in the form of a non-woven structure made of a polymer, for example a biodegradable polymer.

The integrity of this layer or a nonwoven structure is then protected by the functional sleeve during the folding and unfolding process.

Preferably, the medical active ingredient can be contained in a polymer gel formulation, which forms the medical active ingredient layer.

This is advantageous in that the polymer gel formulation gels on contact with blood serum and increases in volume so that the active medical ingredient can be squeezed out between the balloon membrane and the functional sleeve via their passage openings during balloon unfolding and thus transferred efficiently into the hollow organ wall.

The integrity of this gel layer is also protected by the functional sleeve during the folding process, storage and transportation to the site of action.

It is intended that the balloon and the functional sleeve are folded together and unfolded in the region of a blood vessel. After vessel dilation by cushion-like balloon dilation and active substance transfer into the vessel wall in the area of the passage openings and also via the pores and thus over the entire circumferential wall of the functional sleeve, the functional sleeve and the balloon are folded together again and removed.

Preferably, the functional sleeve can be made of a stretch-resistant polymer film, e.g. UHWPE polyethylene or non-compliant Pebax®.

The balloon itself can, for example, be made of semi-compliant or compliant Pebax®.

The through-openings can be designed as slots or elongated openings, in particular axial slits or sinusoidal axially oriented slits and/or as approximately rectangular or approximately elliptical or approximately circular windows or window-like openings in an otherwise (except for the pores, if present) continuous flat circumferential wall of the functional sleeve.

Preferably, the through openings have rounded corners to prevent cracking due to notching.

In addition, two or three or four or five or more rows of (preferably axially oriented) slits can be arranged along the longitudinal axis of the sleeve.

In addition and/or alternatively, the sleeve can be provided with windows over sections or in sections or over its entire surface.

Between two or more adjacent slits extending in the axial direction, predetermined tear points can be formed in order to combine the advantages of a functional sleeve that is as closed as possible with the advantages of greater cushion formation during use when storing and transporting the balloon catheter device.

By providing axial predetermined tear lines in the area between two or more neighboring axial slits, a larger cushion formation is possible, even if only short axial slits are provided.

Axially oriented slit-like through-openings increase cushion formation (i.e. outward bulging of the balloon membrane), whereas tangentially oriented slit-like through-openings practically do not contribute to cushion formation (relative constriction of the balloon membrane). The physical explanation is provided by the so-called kettle formula, according to which the tangential wall stress acting perpendicular to the axial slits of the functional sleeve during balloon dilation is twice as high as the axial wall stress. Axial slits are widened under internal pressure, and this effect is cumulative when grouped around the circumference. Tangentially running slits, on the other hand, are hardly widened at all.

In the area of the through-opening, the functional sleeve forms a corresponding first functional area for cushion formation. The active ingredient is released via the second functional area, which either corresponds to the first or preferably comprises the entire circumferential wall of the functional sleeve including the through openings, provided the functional sleeve has pores.

The medical active ingredient layer with a medical active ingredient can be arranged between the functional sleeve and the balloon, whereby the medical active ingredient layer is formed as

- a coating of the balloon membrane (e.g. by dip coating) of a polymer, in particular a biodegradable polymer (or a combination of polymers) and a medical agent, and/or
- a polymer fleece sprayed onto the balloon membrane, in particular a biodegradable polymer fleece with the medical active ingredient, and/or
- a tubular intermediate sleeve with a nonwoven structure of, in particular biodegradable, polymer and the medical active substance, wherein the medical active substance then being embedded in microcompartments between the polymer fibers, and this being advantageously in conjunction with corresponding window-like passage openings, and/or
- wherein the active medical ingredient is contained in a polymer gel formulation as an active ingredient layer.

The active medical ingredient can thus be contained in a polymer gel formulation which dries after coating the balloon membrane with the evaporation of the solvent, is stored dry with the balloon and gels and increases in volume on application through contact with water or blood serum, whereby pure hydrogels or combinations with oleogels (organogels) may be used.

The functional sleeve arranged over the medical active ingredient thus also serves to protect the active ingredient layer when the balloon is folded in for storage and subsequent transportation to the site of action, so that in the event of liquid contact and balloon dilation, the polymer containing the active ingredient, in particular biodegradable polymer, can be pressed outwards in the area of the through-openings of the sleeve (windows, slits and pores) and applied into a vessel wall.

This active ingredient transport by squeezing through the unfolding balloon membrane through the through openings of the functional sleeve onto its outer surface is particularly effective if the active medical ingredient is contained in a polymer gel formulation that gels and increases in volume on contact with blood serum. After the gel layer has increased in volume, the compression by the balloon membrane causes the gel to be pressed through the passage openings of the sleeve into the hollow organ wall.

If the medical active ingredient layer is formed with biodegradable polymer nanofibers, these detach from the balloon in the area of the passage openings during balloon dilation and form (micro) flakes, which are then pressed against the hollow organ wall (especially the vessel wall).

After balloon deflation, the gel layer or fibers adhere to the hollow organ wall, whereby the active ingredient is trapped in the gel or in the degradable fibers and, in the course of biological degradation of the gel or fibers, provides the therapeutically effective active ingredient level for a critical period of time in contact with the hollow organ wall and at the same time also partially seals the longitudinal cracks in the hollow organ wall that occur after balloon dilation. In this way, the release of the active ingredient and its concentration can be optimally adjusted to the application over time.

The therapeutically required time phase is covered with a therapeutically effective dosage level by releasing the active ingredient via the degradation of the biodegradable gel or the polymer nanofibers. The biodegradation of the gel or the degradation of the fibers and thus the release of the active ingredient should be completed when the critical phase is over so that no permanent residues remain in the vessel.

In the context of the present invention, the term "biodegradable" means that contact of the polymer gel or the polymer nanofibers with body fluid and a hollow organ wall (specifically: blood and vessel wall) induces a decomposition or degradation process of this polymer.

Preferably, the folding of the tubular functional sleeve can be designed as pleating or the sleeve can be pleated. In the context of the present invention, "pleating" is understood to mean folding the sleeve into 2 to 5 (preferably 3) folds of equal size distributed evenly around the circumference (preferably 3×120°) and running in the axial direction, the folds being wound evenly and in the same direction around the longitudinal axis of the balloon catheter and applied to the latter. Pleating makes it possible to reduce the outer diameter of the tubular sleeve in the non-deployed state.

As biodegradable polymer, first and/or second polymer nanofibers can be provided as biodegradable polymer.

The first polymer nanofibers can be made of slowly degradable polymer fibers (PL). The second polymer nanofibers can be formed from rapidly degradable polymer fibers (PS).

Preferably, an active ingredient may only be incorporated into the slowly degradable polymer (PL). An anticoagulant such as heparin or an anticoagulant may also be incorporated into the rapidly degrading polymer (PS).

The degradable polymer can preferably have hydrophilic and/or lipophilic properties. The rate of degradation depends on the type of polymer (e.g. in the case of PLGA polylactide-co-glycolide) by the ratio of GA to LA (a higher content of LA causes a reduction in hydrophilicity and therefore leads to slower dissolution), the molecular chain length (a high molecular weight or a longer chain length causes slower dissolution), and the hydrophilicity of the side groups (e.g. the methyl side groups in PLA have a hydrophobic effect and thus delay dissolution, or in PLGA a hydrophilic carboxyl group leads to faster dissolution than an ester group).

It is thus intended that the medical active ingredient layer in the area of the through-openings through the biodegradable polymer gels breaks down into multiple spots or parts formed by biodegradable polymer nanofibers into multiple "flakes" or "microflakes", which are flat or planar and adhere to the hollow organ wall.

The biocompatible polymer of the polymer gels or polymer nanofibers can consist of polymers based on lactic acid (polylactide, PLA), glycolic acid (polyglycolide, PGA) and its copolymers (poly(lactide-co-glycolide), -PLGA), as well as poly(ε-caprolactone), polyethylene glycol, polyethylene oxide, polysebacic acid, poly(trimethylene carbonate), poly (ethylene-co-vinyl acetate), poly(1,5-dioxepan-2-one), polyvinylpyrrolidone (PVP), poly-p-dioxanone (PPDX) and their compounds and copolymers or mixtures thereof.

Polymer nanofibers preferably have a fiber diameter of less than one micrometer and preferably in the range from 300 to 2000 nm and in particular in the range from 500 to 1000 nm. In the context of the present invention, the polymer nanofibers may also have a diameter of up to 3 micrometers.

Advantageous embodiments in this respect are described in EP 3 922 217 A1, to which reference is hereby made in full.

The medically active agent can preferably be embedded in a polymer, so that the medically active agent layer is formed, and wherein the medically active agent is preferably an antiproliferative, e.g. sirolimus, or other Limus derivatives or paclitaxel (PTX) or a long-term stable depot progestogen, e.g. etonogestrel, levonorgestrel or an antiprogesterone, e.g. mifepristone or a spermicide, e.g. nonoxinol 9 or a cytostatic agent, e.g. mitomycin, capecitabine or methotrexate (MTX).

The functional sleeve can have a smaller cross-section at a proximal and/or a distal end than the rest of the sleeve, with a proximal and/or a distal approximately conically tapering section preferably being provided.

By reducing the cross-section of the functional sleeve, it can be secured against slipping on the balloon.

Conventional balloons tend to expand more in their distal and proximal sections ("dog-bone") during unfolding, which can particularly traumatize the vessel wall there. In the embodiments of the balloon catheter device according to the invention, it is therefore advantageous to dispense with window- or slit-shaped through-openings of the functional sleeve in the proximal and distal sections immediately adjacent to the balloon shoulders in order to prevent dog-bone deformation of the balloon during unfolding.

Furthermore, the functional sleeve can be connected to the catheter shaft of the balloon catheter via proximal and/or distal tab elements.

This also prevents slippage and, in particular, makes it easier to insert the sleeve into the balloon catheter.

The tubular functional sleeve may have a tangential and/or an axial support layer, wherein the tangential support layer is formed by polymer nanofibers with higher strength and/or by an additional polymer layer (e.g. by a laser-cut tubular, degradable polymer semi-finished product, or by a layer formed by means of melt electrospinning writing MEW) and/or in that the functional sleeve has tangentially circumferential and equally spaced axial support struts which are preferably arranged outside the functional sleeve in the region of the inner folding lines.

This type of structural design allows the stiffness of the functional sleeve to be adjusted or improved in the axial and tangential directions.

The coating of the balloon membrane by dip coating or as a sprayed-on polymer fleece or as a sleeving intermediate sleeve can have adhesive properties.

The adhesive properties of the polymer component containing the active ingredient promote adhesion to the hollow organ wall. In concrete terms, this means that the portions of the medical active ingredient layer pressed out via the opening of the functional sleeve adhere to the inner wall of a hollow organ during unfolding.

The sleeve can be bonded to the balloon membrane, e.g. by spot gluing or polymer welding, whereby the connection points are preferably arranged on the inner fold lines of the balloon membrane.

The functional sleeve is preferably made of a low-stretch polymer whose stretchability is lower than the stretchability of the balloon membrane of the balloon.

A total area of the through-opening, if these are designed as slits, can be at least 10 percent or at least 15 percent or at least 20 percent to a maximum of 50 percent or 45 percent or 40 percent or a maximum of 35 percent and in particular a maximum of 30 percent of the total area of the functional sleeve, or a total area of the through openings, if these are designed as window-like openings, can be at least 30 percent or at least 35 percent or at least 40 percent or at least 45 percent or at least 50 percent to 85 percent or a maximum of 80 percent or 75 percent or a maximum of 70 percent of the total area of the functional sleeve.

In addition, an outer protective cover can be arranged on the functional sleeve in the initial state.

Such a film-like protective cover prevents blood contact and thus prevents thrombus formation during insertion of the sleeve. At the implantation site, the protective cover can then be removed by pulling it back or by tearing it as a result of unfolding. In addition, the stability of the folding of the sleeve for transportation on the balloon catheter can be supported by an adhesive surface treatment of the outer surface of the sleeve.

Furthermore, according to the invention, a method for producing a functional sleeve for a balloon catheter device as described above is provided. This comprises the following steps:

Blow molding of a tubular polymer blank in a tempered metallic mold to the diameter of an inner circumferential wall, Demolding and cutting to length in the area of sleeve shoulders, Mounting the sleeve on a retaining core, whereby this can also consist of a unfoldable wire mesh that can adapt to both the sleeve unfolding diameter and the smaller diameter of the sleeve shoulders, Cutting, in particular laser cutting of through-holes in the sleeve to form the functional sleeve.

In addition, a method for manufacturing a balloon catheter device as disclosed above is provided according to the invention. This comprises the following steps:

Application of a medical active substance layer to an outer sleeve wall of a preferably pre-folded balloon of a balloon catheter device in the expanded state of the balloon, Application (axial mounting) of a pre-folded functional sleeve onto/over the dried active ingredient layer with the balloon being deflated, whereby the orientation is such that the folds of the balloon and sleeve lie inside each other, joining of the functional sleeve and the balloon (chemical, material-locking connection: welding, gluing), uniform folding and wrapping of the balloon together with the functional sleeve around a longitudinal axis of the balloon catheter device for storage until application.

The polymer gel solution can be applied to the balloon or to a cylindrical molded body (separate fleece) by spraying with an air jet (airspraying) or by spinning in an electric field (electrospinning) and/or by a combination thereof (electrostatic airspraying) and/or by dipping in a solution (dip coating) and/or by applying a continuous melt strand (melt electrospinning writing) or applied discontinuously by means of 3D printing.

In addition, a release layer can be applied to the balloon membrane or to the support of the fleece before the mixture is applied.

The provision of an appropriate separating layer facilitates the subsequent detachment of the active ingredient layer from the balloon membrane or support.

The advantages of the methods according to the invention correspond analogously to the advantages explained above with reference to the balloon catheter device according to the invention.

For all applications of the balloon catheter device according to the invention in hollow organs, an atraumatic expansion of constrictions can be achieved by the cushion-shaped segmentation of the outer contour. Possible active ingredient applications can be briefly summarized as follows, depending on the hollow organ application:

Antiproliferative agents such as limus derivatives (e.g. sirolimus) or paclitaxel (PTX) are suitable for use in blood vessels as active substances for transfer into the vessel wall to reduce an excessive wall reaction (intimal hyperplasia)

Active substances with a contraceptive effect, e.g. long-term stable depot progestogens, such as etonogestrel, levonorgestrel or a suitable antiprogesterone, such as mifepristone or a spermicide, such as nonoxinol 9, are suitable for application in the fallopian tube. In principle, an application with a contraceptive agent in the area of the ductus deferens (vas deferens) is also possible.

Cytostatic drugs such as mitomycin, capecitabine or methotrexate (MTX) can be used to treat carcinomas in hollow organs, e.g. in the bile ducts.

Other possible applications include other hollow organs such as the pancreatic duct, the urinary tract, lymphatic vessels such as the thoracic duct, the tracheobronchial system, the nasolacrimal duct, the Eustachian tube or the gastrointestinal tract.

Furthermore, medical and therapeutic methods for the treatment of hollow organs with the balloon catheter device according to the invention are provided.

For use in the blood vessel, the balloon catheter device according to the invention is intended to serve as a carrier for antiproliferative agents such as limus derivatives and thus ensure their transfer with a longer-term contact to the vessel wall.

When used in blood vessels, Limus derivatives have a much more favorable biological effect than paclitaxel. However, they are difficult to transfer into the vessel wall with conventionally coated balloons by a single short balloon contact, as they adhere much less well than paclitaxel crystals which are impaled into the vessel wall. With the balloon catheter device according to the invention, the polymer drug layer is pressed onto or into the vessel wall as "gel spots" or "micro-flakes" via the through-openings of the functional sleeve.

When applying the balloon catheter device according to the invention in the region of the fallopian tubes, active substances with a contraceptive effect such as long-term stable depot progestogens, e.g. etonogestrel, levonorgestrel or a suitable antiprogesterone, e.g. mifepristone or a spermicide, e.g. nonoxinol 9 can be provided. In principle, application with a contraceptive agent in the area of the ductus deferens (vas deferens) is also possible.

For the therapy of carcinomas in hollow organs, e.g. in the bile ducts, cytostatic agents such as mitomycin, capecitabine or methotrexate (MTX) can be provided as medically active substances for the balloon catheter device according to the invention.

Other possible applications of the balloon catheter device include other hollow organs such as the pancreatic duct, the urinary tract, lymphatic vessels such as the thoracic duct, the tracheobronchial system, the nasolacrimal duct, the Eustachian tube or the gastrointestinal tract.

Figure 17:
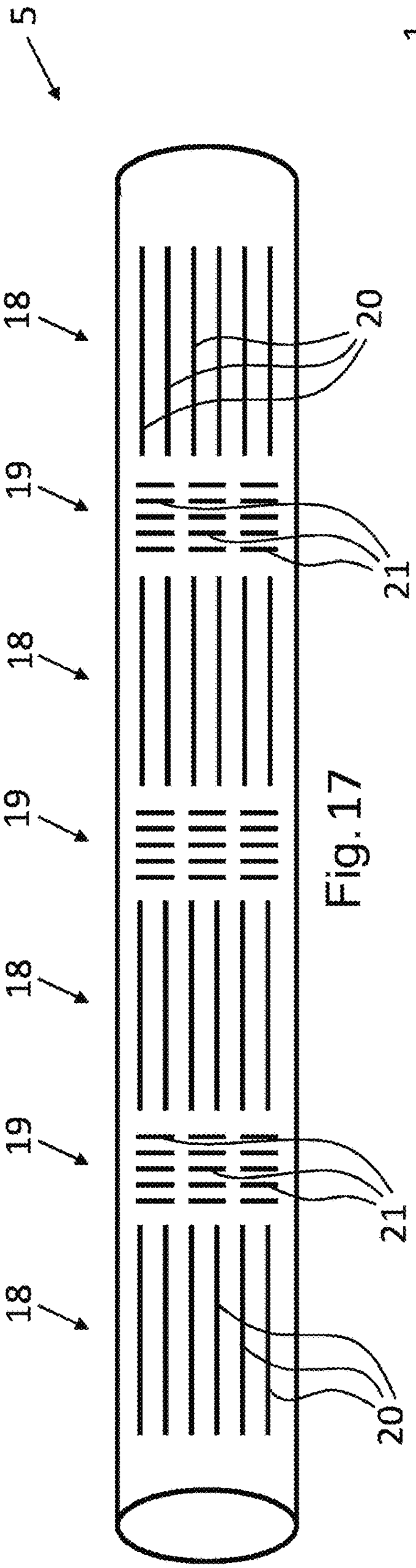
Figure 18:
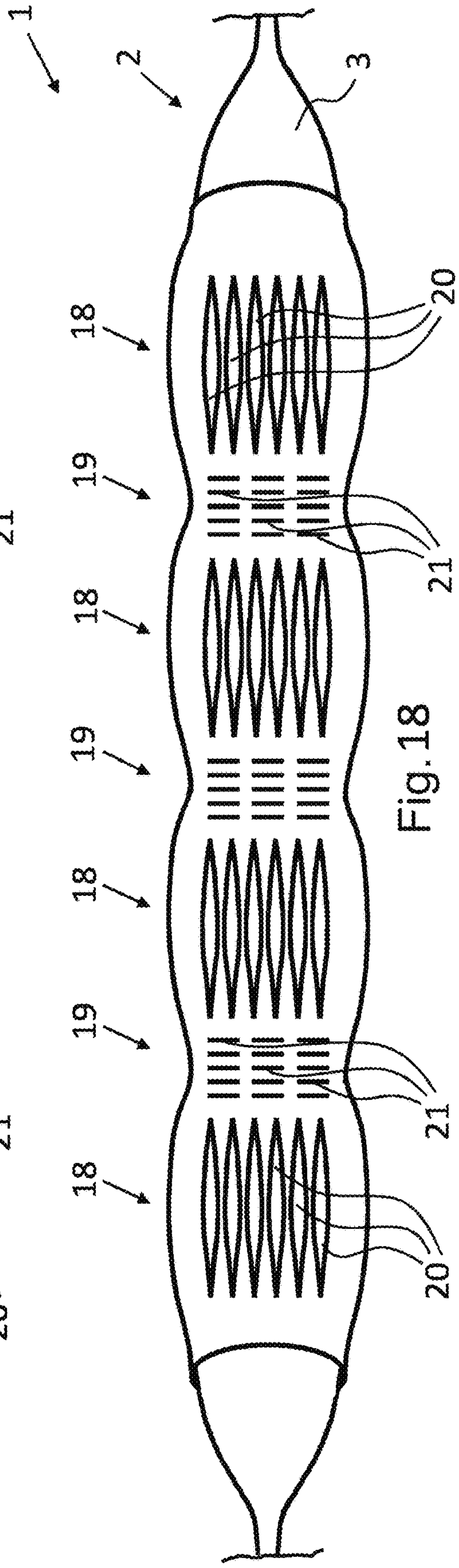

The present invention is described below with reference to several embodiments shown in the figures. These show in FIG. 1 is a schematic side view of a balloon catheter device according to the invention according to a first embodiment, with window-like through openings, FIG. 2 a schematic lateral representation of the balloon catheter device according to the invention according to a second embodiment, with window-like through openings and conically tapering sections at the proximal and distal ends, FIG. 3 a schematic lateral representation of the balloon catheter device according to the invention according to a third embodiment, with triangular window-like through openings, FIG. 4 a schematic lateral representation of the balloon catheter device according to the invention according to a fourth embodiment, with three rows of slits consisting of axial slits extending in the longitudinal direction and proximal and distal tab elements, FIG. 5 a schematic lateral view of the balloon catheter device according to the invention according to a fifth embodiment, with three rows of slits and a pattern of pores (perforations) (not shown) and conically tapering sections at the proximal and distal ends, FIG. 6 a schematic lateral representation of the balloon catheter device according to the invention according to a sixth embodiment, with three rows of slits, conically tapering sections at the proximal and distal ends and support struts extending in the axial direction, FIG. 7 a schematic lateral representation of the balloon catheter device according to the invention according to a sixth embodiment with a segmented structure of interconnected circumferential rings, FIG. 8 a schematic representation of a folding pattern (pleating in 3 folds) of the functional sleeve, FIG. 9 a schematic representation of a third of a circumferential segment, corresponding to the lateral surface of a fold, in the unwound state, FIG. 10 a further embodiment of a third of a circumferential segment, corresponding to the lateral surface of a fold, in the unwound state, FIG. 11 a schematic representation of a functional sleeve section with axially oriented slits of a functional sleeve, which allows a clear cushion-like protrusion of an underlying balloon membrane during expansion, FIG. 12 a functional sleeve section with tangentially oriented slits of a functional sleeve, which allows a slight protrusion of an underlying balloon membrane during expansion, FIG. 13 a further illustration of a sectional slit pattern of slits of a functional sleeve, FIG. 14 a further illustration of a sectional slit pattern of slits of a functional sleeve, FIG. 15 a schematic representation of grouped axial slits and holes (pores) in the functional sleeve, FIG. 16 a schematic representation of a combination of grouped axial slits and holes with intentional crack formation between closely adjacent slits during balloon dilation, FIG. 17 a schematic top view of an advantageous embodiment of the functional sleeve of the balloon catheter device according to the invention, and FIG. 18 a schematic representation of a balloon catheter device according to the invention with a functional sleeve as shown in FIG. 17.

A balloon catheter device 1 according to the invention is described in more detail below with reference to a first embodiment (FIG. 1).

The balloon catheter device 1 is formed for atraumatic treatment of hollow organs and comprises a balloon catheter 2 (shown without proximal catheter shaft) with a balloon 3. A layer of active medical ingredient 4 is applied to a circumferential wall of the balloon 3.

The medical active ingredient layer 4 is formed as a coating of a balloon membrane of the balloon 3, whereby the medical active ingredient is contained in a polymer gel formulation.

Alternatively, the medical active ingredient layer 4 can be designed as a biodegradable polymer fleece sprayed onto the balloon membrane with compartments or micro-compartments in which the medical active ingredient is embedded.

Alternatively, the medical active ingredient layer 4 may be formed as a tubular intermediate sleeve with a non-woven structure made of biodegradable polymer with micro-compartments or compartments in which the medical active ingredient is embedded.

A functional sleeve 5 is arranged on the medical active ingredient layer 4 or on the balloon 3 of the balloon catheter 2, which is connected to the balloon 3 of the balloon catheter 2.

In particular, the sleeve 5 is connected to the balloon membrane or balloon 3 with a material bond. The connection is made, for example, by spot welding, adhesive bonding over a large area or by adhering a gel containing an active ingredient between the balloon membrane and the functional sleeve. Punctiform or linear connections are preferably arranged along inner fold lines.

According to the first embodiment, the functional sleeve 5 is approximately tubular or cylindrical and is made of a polymer with a low stretchability.

Approximately rectangular through-openings 6 are provided in the functional sleeve 5, which are bounded by flat sections or flat struts 7.

In this case, it is intended that approximately the entire surface of the functional sleeve 5 has the through-opening 6 or the through-opening 6 is arranged over almost the entire surface of the functional sleeve 5.

In an initial state, the functional sleeve 5 is folded together with the medical active substance layer 4 and the balloon 3 about a longitudinal axis of the sleeve, wherein the folding is directed as pleating about a longitudinal axis of the sleeve and can be unfolded in a final state to lie against an inner wall of a hollow organ.

According to all embodiments, the through openings have rounded corners.

Furthermore, the functional sleeve 5 has pores 20 (not shown in FIG. 1) in the area of its struts 7 or on its entire circumferential wall.

Figure 2:
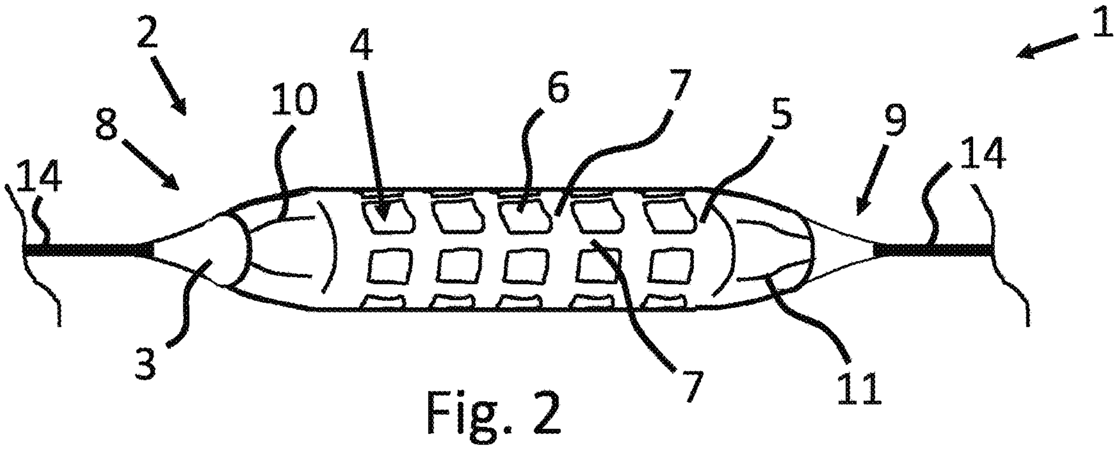

In the following, the balloon catheter device 1 according to the invention is described in more detail with reference to a second embodiment (FIG. 2). Unless otherwise described, the second embodiment, as well as the other embodiments that follow, essentially corresponds to the balloon catheter device 1 according to the first embodiment. Identical technical features are marked with the same reference signs.

According to the second embodiment, the functional sleeve 5 of the balloon catheter device 1 has a smaller cross-section at a proximal and at a distal end 8, 9 than the rest of the functional sleeve. These sections are referred to as the proximal and distal conical sections 10, 11. The proximal cone-shaped section 10 and the distal cone-shaped section 11 are designed to prevent axial displacement of the functional sleeve 5 on the balloon 3.

Figure 3:
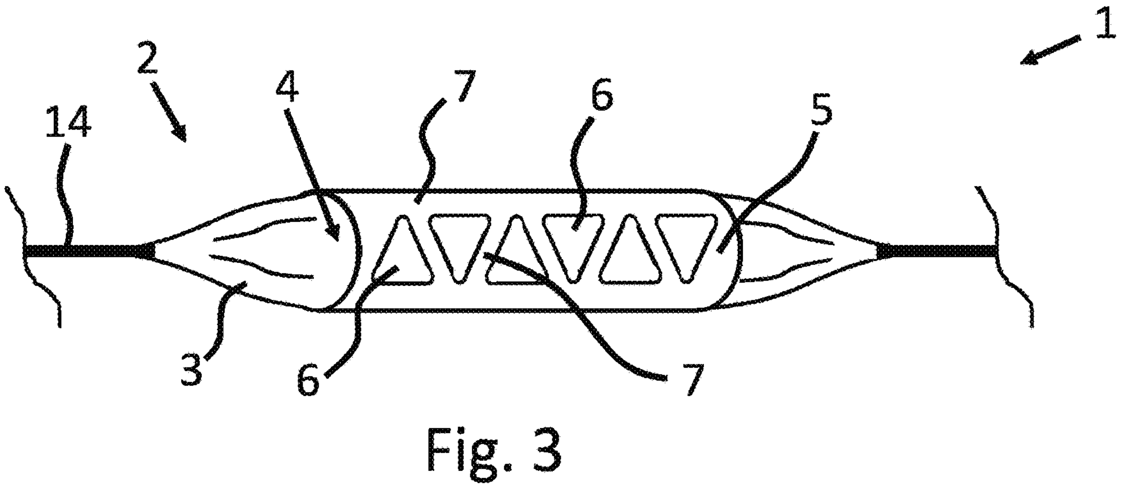

According to a third embodiment, the through openings 6 are roughly triangular in shape (FIG. 3).

Figure 4:
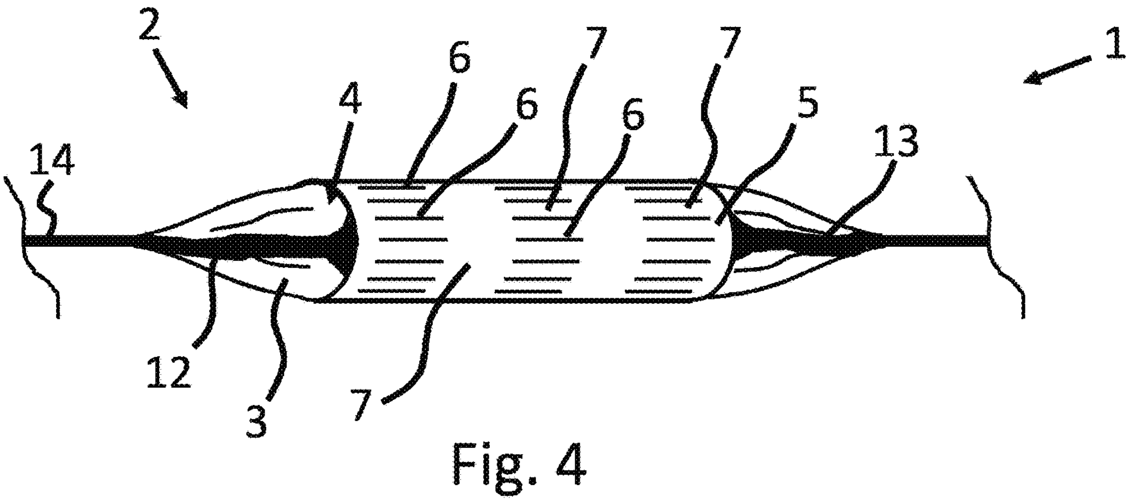

According to a fourth embodiment, the through-openings 6 are designed as slits extending in the axial direction, with three rows of tangentially circumferential axial slits being provided in the present embodiment (FIG. 4).

In addition, according to the fourth embodiment of the balloon catheter device, the functional sleeve 5 is connected to a catheter shaft 14 of the balloon catheter 2 via proximal and distal tab elements 12, 13.

In this way, the functional sleeve 5 is secured against slipping on the balloon 3 of the balloon catheter device 1. In addition, the tab elements 12, 13 facilitate the insertion of the functional sleeve 5 together with the balloon catheter 2 into a guide catheter or a sleeve.

Figure 5:
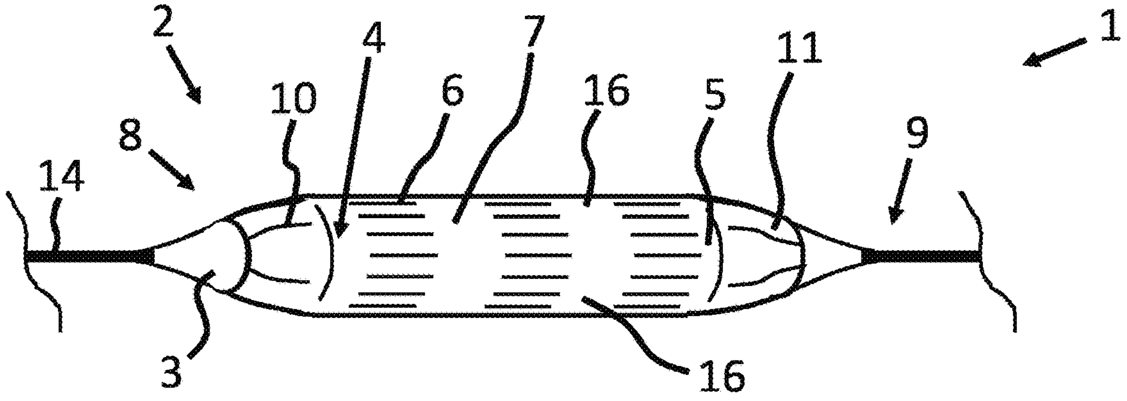

According to a fifth embodiment, which essentially corresponds to the fourth embodiment, the through openings 6 are also in the form of axial slits, wherein the functional sleeve also comprises the proximal conical section 10 and the distal conical section 11 and has a pattern of pores (perforations; not shown) in the region of the struts 7 (FIG. 5).

Figure 6:
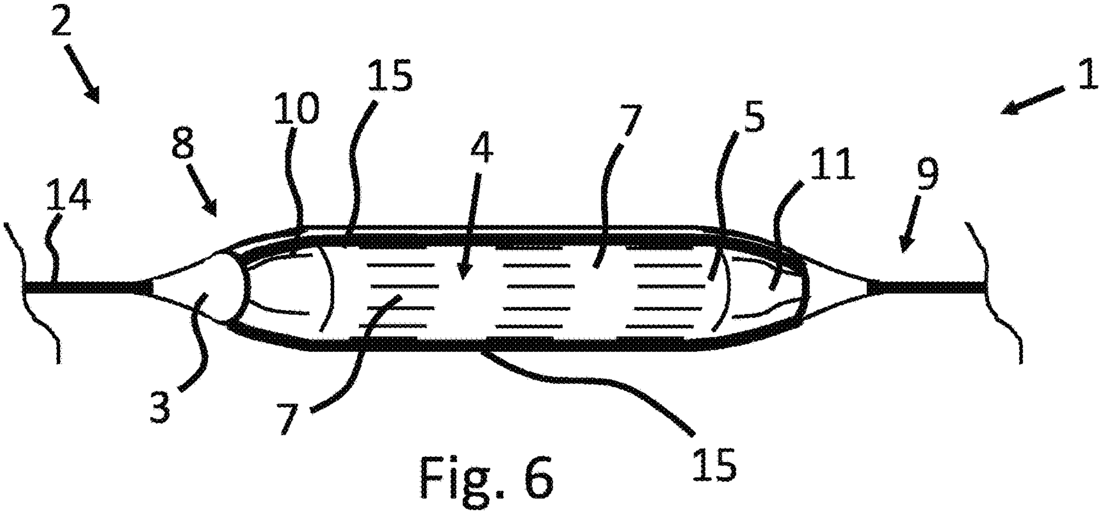
Figure 7:
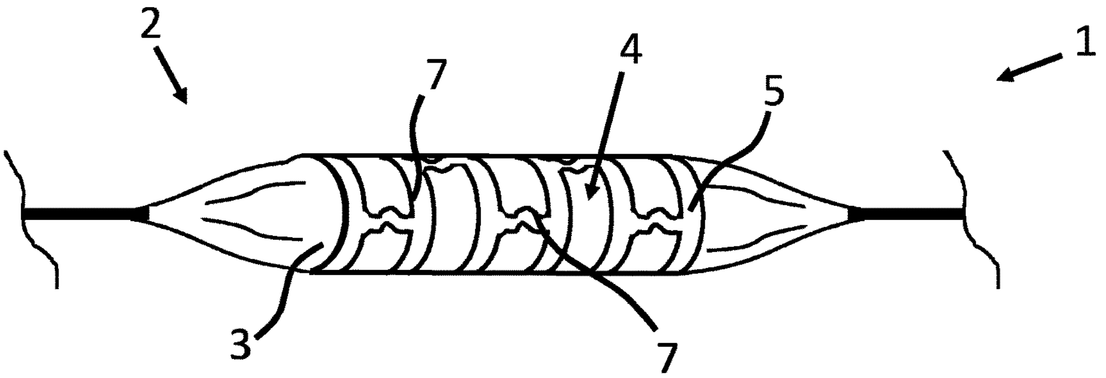

According to a sixth embodiment, which essentially corresponds to the fifth embodiment, the functional sleeve 5 has three axial struts 15, which extend over approximately the entire length of the functional sleeve 5 in the axial direction and are arranged tangentially circumferentially at approximately the same distance from one another at an angle of approximately 120° (FIG. 6). According to this embodiment, three axial support struts are provided in order to increase the rigidity of the functional sleeve in the axial direction. However, two or four or five or more axial struts 15 can also be provided.

The through-openings designed as slits according to the fourth, fifth and sixth embodiments can be connected to each other in the axial direction via predetermined tear points 17 (FIG. 16), so that when a balloon expands, several adjacent axial slits connect to form a common axial slit and enable a larger cushion to be formed in this area.

According to a seventh embodiment, the through-openings 6 of the functional sleeve are in the form of tangentially circumferential recesses or slits, which are, however, interrupted at least once by axially extending struts 7.

As shown above, the technical features of the present invention can be combined with one another as desired with regard to the geometric or structural design of the through openings 6, the struts 7, the conical sections 10, 11, the lug elements 12, 13, the axial struts or tangential struts or also an axial or a tangential support layer and the predetermined tearing points 17, insofar as technically possible and expedient.

Various or different configurations of the through-openings 6, insofar as these are designed as slits, are shown in FIGS. 11 to 16.

Figure 11:
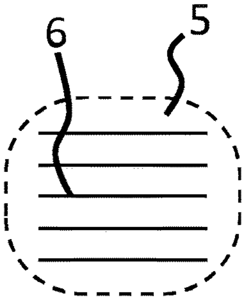

Preferably, the slits only extend in the axial direction (FIG. 11).

Figure 13:
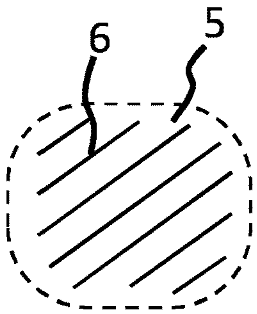

However, the slits can also be inclined relative to the axial direction (FIG. 13).

Figure 14:
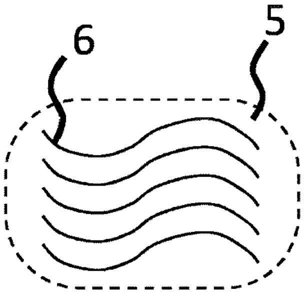

In addition, the slits can also be wavy (FIG. 14).

Figure 12:
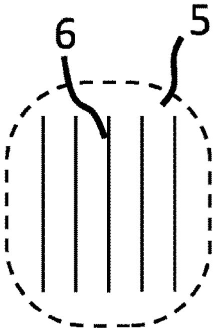

Furthermore, the slits can also extend in a tangential direction according to a non-advantageous embodiment, which does not result in any significant cushioning of an expanded balloon membrane located underneath (FIG. 12).

Figure 15:
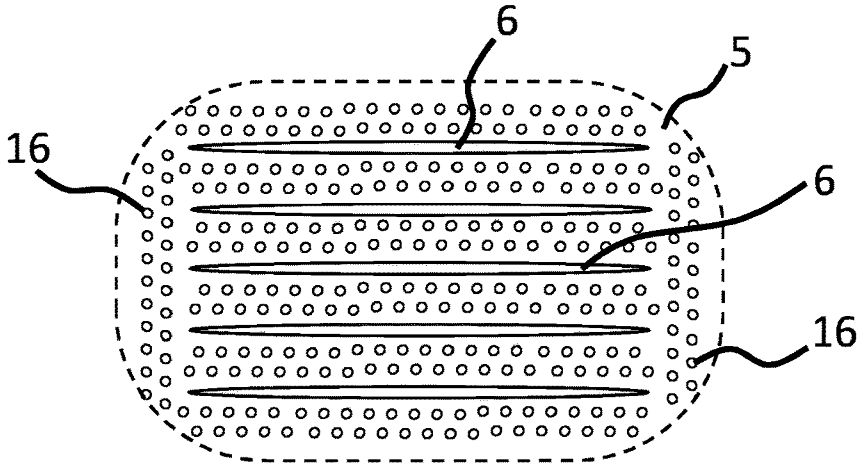

In the area of the struts 7 and in particular also in the area between the axial slits, pores 16 are distributed over the entire circumferential wall of the functional sleeve 5 (FIG. 15).

Figure 16:
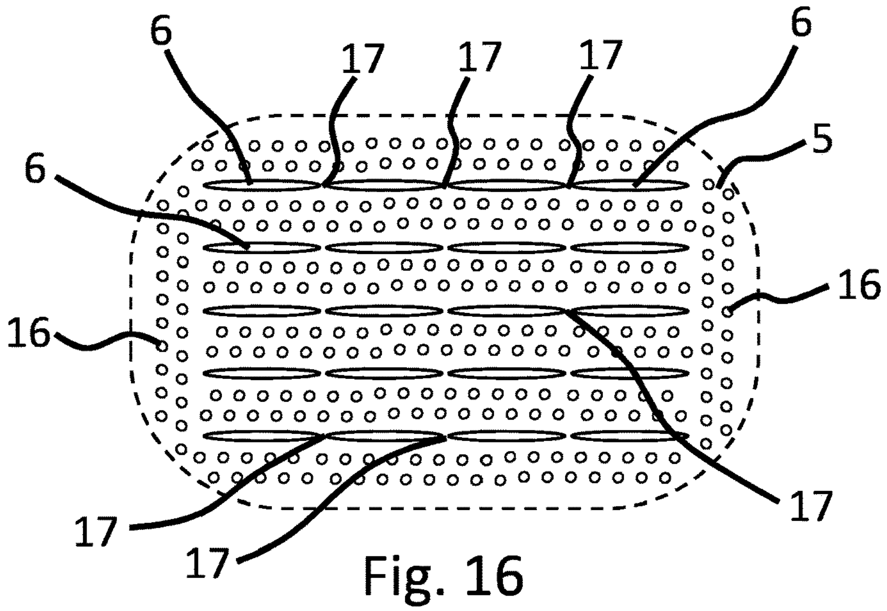

According to such an embodiment, the slits can also be shorter, in which case, for example, four axial slits can be connected to each other via predetermined tear points 17 when the balloon 3 expands (FIG. 16).

Figure 8:
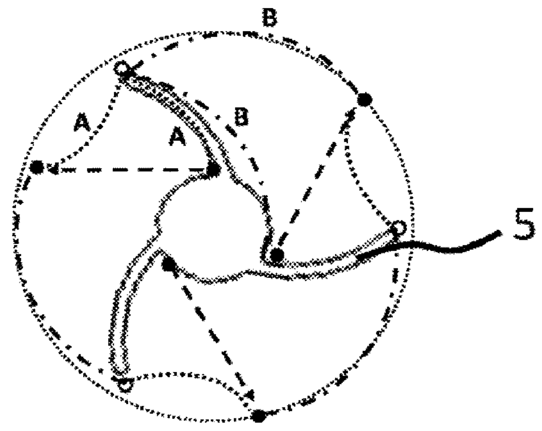
Figure 9:
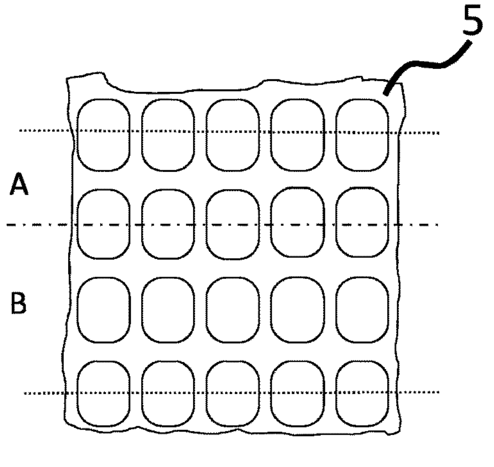
Figure 10:
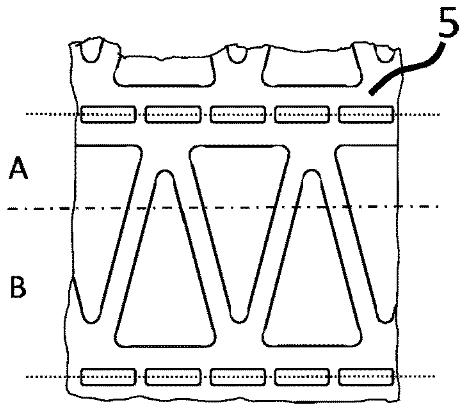

The balloon 3, the medical active ingredient layer 4 and the functional sleeve 5 of the balloon catheter device 1 are folded or pleated around a longitudinal catheter axis in an initial state. During folding, for example, three folds of equal size are provided, evenly distributed around the circumference and running in the axial direction. The folds extend along a first fold line A and a second fold line B (FIGS. 8 to 10).

The folds are wound evenly and in the same direction around the longitudinal axis of the balloon catheter and attached to it.

Furthermore, according to the invention, a method for producing a functional sleeve for a balloon catheter device as described above is provided. This comprises the following steps:

- Blow molding of a tubular polymer blank in a tempered metallic mold to the diameter of an inner circumferential wall,
- Demolding and cutting to length in the area of sleeve shoulders,
- Mounting the sleeve on a retaining core, which can also consist of a unfoldable wire mesh that can adapt both to the sleeve unfolding diameter and to the smaller diameter of the sleeve shoulders,
- Cutting, in particular laser cutting of through-holes in the sleeve to form the functional sleeve.

In addition, a method for manufacturing a balloon catheter device as described above is provided according to the invention. This comprises the following steps:

- Application of a medical active substance layer to an outer sleeve wall of a preferably pre-folded balloon of a balloon catheter device in the expanded state of the balloon,
- Application (axial mounting) of a pre-folded functional sleeve onto/over the dried active agent layer with a deflated balloon, whereby the orientation is such that the folds of the balloon and sleeve lie one inside the other, bonding of the functional sleeve and the balloon (welding, gluing, adhesive active agent layer),
- uniform folding and wrapping of the balloon together with the functional sleeve around a longitudinal axis of the balloon catheter device for storage until use and for transportation to the site of action.

The polymer gel solution can be applied to the balloon or to a cylindrical molded body (separate fleece) by spraying with an air jet (air spraying) or by spinning in an electric field (electrospinning) and/or by a combination thereof (electrostatic air spraying) and/or by dipping in a solution (dip coating) and/or by applying a continuous melt strand (melt electrospinning writing) or applied discontinuously by means of 3D printing.

In addition, a release layer can be applied to the balloon membrane or to the backing of the fleece before the mixture is applied.

The provision of an appropriate separating layer facilitates the subsequent detachment of the active ingredient layer from the balloon membrane or the fleece from the support.

In the following, a preferred embodiment of a balloon catheter device 1 according to the invention for gentle cushion-like balloon dilation of the hollow organ and simultaneous application of active substance into the hollow organ wall is described in more detail (FIG. 17). Unless otherwise described, this balloon catheter device 1 has all the features of the balloon catheter devices described above. Identical technical features are marked with the same reference signs.

This balloon catheter device 1 comprises the balloon catheter 2 with the balloon 3. A medical agent layer 4 is applied to the circumferential wall of the balloon 3.

Furthermore, the functional sleeve 5 is arranged on the balloon catheter 2, whereby the functional sleeve 5 is connected to the balloon catheter 2 essentially over its entire length. A distributed punctiform, a planar or an essentially planar connection can be provided.

However, a connection along connection points or lines of the welded sheets, produced by plastic welding, in particular polymer welding, is preferred. Corresponding connection points or lines are preferably located on fold lines of the sleeve and the balloon, in particular on inner fold lines.

The functional sleeve 5 has a higher rigidity than the balloon 3, or a higher modulus of elasticity with approximately the same wall thickness.

In the functional sleeve 5, axial sections 18 and tangential sections 19 are arranged alternately at a distance from each other in the longitudinal direction.

One of the axial sections 18 is initially formed at a proximal end of the functional sleeve 5.

Axial slits 20 are formed in the axial section 18 tangentially or radially circumferentially and at approximately the same distance from each other extending in the axial direction. The axial slits 20 have approximately the same length in the axial direction and are aligned with one another in the tangential direction.

The first axial section 18 is followed by a first tangential section 19.

The axial sections 18 are arranged at a distance from the tangential sections 19 in the longitudinal direction.

Several tangential slits 21 extending transversely to the longitudinal direction or extending in the tangential direction are formed in the tangential section 19. The tangential slits 21 are equally spaced from one another in the axial direction and extend tangentially or radially around the circumferential wall of the functional sleeve 5.

The balloon 3 of the balloon catheter 2 and the functional sleeve 5 connected to it are folded and pleated together around a longitudinal axis of the balloon catheter device 1.

For atraumatic treatment of hollow organs, the balloon catheter device 1 is then provided in the area of a hollow organ to be treated.

The balloon 3 of the balloon catheter 2 is then expanded so that the balloon 3 unfolds together with the functional sleeve 5 connected to it.

This is followed by expansion of the hollow organ with cushion formation of the balloon membrane of the balloon 3 in the area of the tangential slits 21. In the area of the axial slits 20 and the tangential slits 21, the active ingredient is then applied to an inner wall of the hollow organ.

After completion of the hollow organ dilation and application of the active ingredient, the balloon 3 of the balloon catheter 2 is deflated, whereby the balloon 3 and the functional sleeve 5 fold back together along predetermined folding lines that were previously created during folding and pleating. The balloon catheter device 1 can then be removed from the human body.

It can also be provided that the functional sleeve 5 has pores over essentially its entire surface. The active medical ingredient can also be applied through these pores.

According to the present embodiment, it is provided that axial sections 18 are arranged at a proximal and at a distal end of the functional sleeve 5. According to this embodiment, a total of four axial sections 18 are provided, with correspondingly three tangential sections 19 being arranged between the axial sections 18 and at a distance from these.

All embodiments and embodiments of the balloon catheter device according to the invention can be freely combined with each other, provided that this is technically feasible and possible.

LIST OF REFERENCE SYMBOLS

1 Balloon catheter device
2 Balloon catheter
3 Balloon
4 Medical active ingredient layer
5 Functional sleeve
6 Passage openings
7 Striving
8 Proximal end
9 Distal end
10 Proximal conical section
11 Distal conical section
12 Proximal tab elements
13 Distal tab elements
14 Cathetership
15 Axial struts
16 Pores
17 Predetermined tear points
18 Axial section
19 Tangential section
20 Axial slit
21 Tangential slit

The invention claimed is:

1. A balloon catheter device for atraumatic dilation of hollow organs, comprising a balloon catheter with a balloon, a tubular functional sleeve applied to the balloon for directional segmented cushion-like unfolding of the balloon, and wherein the functional sleeve is folded in an initial state together with the balloon about a sleeve longitudinal axis, and wherein the folding of the functional sleeve is directed as pleating about a sleeve longitudinal axis and is unfoldable in a final state for abutting against an inner wall of a hollow organ, and wherein the tubular functional sleeve has planar sections and/or planar struts which delimit through-openings, so that the functional sleeve delimits balloon expansion in sections, wherein the functional sleeve is connected to the balloon in the region of the planar sections and/or the planar struts, wherein the through openings are formed as laser-cut slits, wherein sections with axial slits, which are referred to as axial sections, and sections with tangential slits, which are referred to as tangential sections, are formed alternately in the functional sleeve in an axial direction of the functional sleeve, and wherein the axial sections and the tangential sections are arranged spaced from each another.

2. The balloon catheter device according to claim 1, wherein providing alternately arranged axial sections with corresponding axial slits and tangential sections with corresponding tangential slits results in a constant or essentially uniform widening of a diameter of the sleeve and the balloon in a radial direction.

3. The balloon catheter device according to claim 1, wherein the tangential sections form decoupling sections between the axial sections in order to provide an approximately constant diameter in a radial direction over a substantially entire length of the device in the axial direction, so that the device can be expanded substantially cylindrically in the axial direction.

4. The balloon catheter device according to claim 3, wherein the decoupling sections formed by the tangential sections cause a constriction of the balloon in these areas so that a substantially constant diameter is provided in the axial sections, resulting in a substantially uniform distribution of forces in the radial direction towards the outside during unfolding.

5. The balloon catheter device according to claim 1, wherein the alternately arranged axial sections and tangential sections are formed and arranged at a distance from one another in an axial direction in such that they do not overlap one another, and/or that the axial slits of the axial sections and the tangential slits of the tangential sections are formed and arranged in such that they do not overlap one another in a tangential direction.

6. The balloon catheter device of claim 1, wherein the through- openings are preformed as slits.

* * * * *